(12) United States Patent
Isler (10) Patent No.: US 7,347,573 B1
(45) Date of Patent: Mar. 25, 2008

(54) PORTABLE, FOLDABLE MIRROR

(76) Inventor: Glenn E Isler, 4085 Stratford Blvd., Steubenville, OH (US) 43952-1058

( * ) Notice: Subject to any disclaimer, the term of this patent is extended or adjusted under 35 U.S.C. 154(b) by 0 days.

(21) Appl. No.: 11/581,174

(22) Filed: Oct. 12, 2006

(51) Int. Cl.
*G02B 5/08* (2006.01)
*G02B 7/182* (2006.01)
*F21V 33/00* (2006.01)

(52) U.S. Cl. ............... 359/854; 359/860; 362/138
(58) Field of Classification Search ........ 362/135–138, 362/142; 359/854, 850, 855, 860, 865
See application file for complete search history.

(56) References Cited

U.S. PATENT DOCUMENTS

| | | | |
|---|---|---|---|
| 518,382 A * | 4/1894 | Wiederer | ............... 359/854 |
| 1,451,236 A | 4/1923 | Stanfield | |
| 1,859,592 A * | 5/1932 | Marchand | ............... 362/141 |
| 2,140,069 A | 12/1938 | Bostwick | |
| 2,201,251 A | 5/1940 | Van Patten | |
| 3,533,671 A * | 10/1970 | Huber | ............... 312/227 |
| 4,050,790 A | 9/1977 | Jorwa | |
| 4,119,107 A * | 10/1978 | Pinzone et al. | ............... 132/316 |
| 4,643,544 A | 2/1987 | Loughran | |
| 6,007,206 A | 12/1999 | Chang | |
| 6,347,876 B1 | 2/2002 | Burton | |
| 6,926,416 B2 | 8/2005 | Sawyer | |
| 2006/0245091 A1* | 11/2006 | DeFazio | ............... 359/879 |

FOREIGN PATENT DOCUMENTS

GB  1.015.485  12/1965

* cited by examiner

*Primary Examiner*—Alessandro Amari
(74) *Attorney, Agent, or Firm*—Michael I Kroll (57) ABSTRACT

The Present invention relates to a portable folding mirror. The mirror has a rear mirror panel, a plurality of mirror panels secured to the rear mirror panel. The plurality of mirror panels includes a base mirror panel, and two front mirror panels, wherein each panel is secured to the rear mirror panel by at least one hinge. The plurality of panels have a closed position where they are folded over the rear panel and an open position where they are folded off and away from the base panel. There is a light fixture located at the top of the rear panel to aid the user. Power to the light may be provided by a battery or by an electric cord. A carrying handle can be provided to make it easy to transport the portable mirror.

7 Claims, 12 Drawing Sheets

PORTABLE, FOLDABLE MIRROR

BACKGROUND OF THE INVENTION

1. Field of the Invention

The present invention relates generally to mirrors and, more specifically, to a portable mirror having a plurality of foldable mirror panels, each hingedly attached to a main mirror panel. A light fixture is provided and sits at the top of the device, flush with the folding panels when in the closed position. A sensor is provided between the main panel and the foldable mirror panels and is activated when the panels are moved to an open position. The device provides easy viewing of feet for people inflicted with diseases such as diabetes.

2. Description of the Prior Art

There are other portable mirrors designed for the same purpose. Typical of these is U.S. Pat. No. 1,451,236 issued to Stanfield on Apr. 10, 1923.

Another patent was issued to Bostwick on Dec. 13, 1938 as U.S. Pat. No. 2,140,069. Yet another U.S. Pat. No. 2,201,251 was issued to Van Patten on May 21, 1940 and still yet another was issued on Sep. 27, 1977 to Jorwa as U.S. Pat. No. 4,050,790.

Another patent was issued to Loughran on Feb. 17, 1987 as U.S. Pat. No. 4,643,544. Yet another U.S. Pat. No. 6,007,206 was issued to Chang on Dec. 28, 1999. Another was issued to Burton on Feb. 19, 2002 as U.S. Pat. No. 6,347,876 and still yet another was issued on Aug. 9, 2005 to Sawyer as U.S. Pat. No. 6,926,416. Another patent was issued to Myerberg on Dec. 31, 1965 as UK Patent No. GB1,015,485.

U.S. Pat. No. 1,451,236

Inventor: Earl E. Stanfield

Issued: Apr. 10, 1923

In combination, a main frame, a pair of side frames; hinged thereto; a. pair of resilient U-shaped braces pivotally mounted on the main frame, and a. pair, of apertured plates mounted on the side frames for receiving the braces whereby the side frames may be held in adjusted position in relation to the main frame due to resiliency of the braces.

U.S. Pat. No. 2,140,069

Inventor: Cyrus R. Bostwick

Issued: Dec. 13, 1938

A mirror comprising a main section, auxiliary sections pivotally mounted at opposite ends of the main section for swinging movement from an extended position to a folded position in covering relation to the main section, a handle depending from the main section midway the ends thereof, said auxiliary sections having their free ends meeting in abutting relation to each other over the handle when folded, a stem projecting forwardly from the upper portion of said handle at substantially right angles to the front face of the handle, a latch rotatably mounted upon said stem and having an upper portion for engaging over lower corner portions of the auxiliary sections when folded and a lower actuating arm extending longitudinally of the handle, and a fastener for said latch threaded upon said stem.

U.S. Pat. No. 2,201,251

Inventor: Edith Van Patten

Issued: May 21, 1940

A mirror assembly comprising a central mirror and wing mirrors separate therefrom; cylindrical windowed lamp enclosing housings at the sides of the central mirror, said housings comprising main central members secured on the side edges of and shorter than the central mirror and disposed-symmetrical relative to the top and bottom thereof, sleeves fitted in the ends of the central member of each housing and projecting therefrom whereby to leave portions of reduced diameter exposed beyond the central member, enlarged flanges on the outer ends of the sleeves, and circular bands projecting from the side edges of the wing mirrors and turnably engaging said exposed reduced diameter portions of the sleeves.

U.S. Pat. No. 4,050,790

Inventor: Mildred M. Jorwa

Issued: Sep. 27, 1977

The present invention constitutes a self-styling mirror including four planer surfaces connected along adjacent edges thereof. The two outer surfaces are angularly moveable with respect to the two inner surfaces. The self-styling mirror is secured upon a vertical pole and is vertically moveable up and down the pole. Further, the entire four-mirror system is universally moveable about a universal joint which depends transversely from said vertical member.

U.S. Pat. No. 4,643,544

Inventor: William P. Loughran

Issued: Feb. 17, 1987

A mirror assembly detachably attachable by Velcro loop pile fastener means to an automobile inside rear view mirror and including a row of mirrors that are angularly pivotable respective to each other for reflecting images from a rear and each opposite sideward direction.

U.S. Pat. No. 6,007,206

Inventor: Kwei-Tang Chang

Issued: Dec. 28, 1999

A comb mirror for improving health of a human body is disclosed. A plurality of far infrared ray lamps are installed in the inner space of the comb mirror body, By a first switch within the body, the first switch will control the on and off states of the far infrared ray lamps. A protecting web is installed in front of the inner space for isolating the far infrared ray lamps for providing the user to contact the far infrared rays lamps. Each of two sides of the body is installed with a respect mirror door which may rotate with the body. Each outer surface of the mirror door is installed with a plan mirror. The inner surface of the mirror seat is installed with concave mirror. By opening the mirror door, far infrared ray will be emitted. The concave mirror serves to focus the far infrared ray to the human body.

U.S. Pat. No. 6,347,876

Inventor: Johnnie Burton

Issued: Feb. 19, 2002

A lighted mirror assembly for hands-free viewing of the back and sides of the head while cutting or styling hair. The lighted mirror assembly includes a base, a pole extending from the base, a mirror assembly with a plurality of mirrors, and a plurality of light assemblies.

U.S. Pat. No. 6,926,416

Inventor: Bradley Sawyer

Issued: Aug. 9, 2005

The present invention provides a multi-view mirror having a mirror frame including an inwardly disposed center and two outwardly disposed mirror mounting elements attached to the frame on opposite sides of the center. The multi-view mirror includes a first mirror having an outward edge pivotally mounted to one of the mounting elements of the frame and an inward edge disposed inwardly of the outward edge near the center of the frame and a second mirror having an outward edge pivotally mounted to one of the mounting elements of the frame and an inward edge disposed inwardly of the outward edge near the center of the frame. The first mirror and second mirror are angularly positionable relative to the frame wherein at least one of the first and second mirrors are pivoted about one of the mounting elements to form a generally angled mirror.

U.K. Patent Number GB1015485

Inventor: Michael Myerburg

Issued: Aug. 3, 1962

A make-up mirror has a vertical row of electric light bulbs B at each side and a horizontal row at the top, the bulbs being positioned to illuminate the face of the user directly, and by reflection from the mirror panel, simultaneously, and being low wattage, large surface incandescent bulbs with a matt exterior light-diffusing coating, to provide shadowless illumination. As shown, a central panel 1 and hinged side panels 2 consist of mirrors 4, 7 supported on plywood backings and the bulbs are mounted by sockets 10 secured by screwed angle irons 12 in bores 11 in a head 6 and posts 9, secured to the panels. A flexible cable 14 connects the bulbs in parallel and carries a switch S and plug connection 15. The bulbs are 15 watt capacity, are spaced a bulb diameter apart, and provide one square inch of bulb surface for each three watts, danger of burning of the face, if brought into contact with a bulb in close make-up work, being eliminated.

While these portable mirrors may be suitable for the purposes for which they were designed, they would not be as suitable for the purposes of the present invention, as hereinafter described.

SUMMARY OF THE PRESENT INVENTION

A primary object of the present invention is to provide a portable lighted mirror having a plurality of foldable mirror panels.

Another object of the present invention is to provide a portable lighted mirror having a plurality of foldable mirror panels each hingedly attached to a main mirror panel.

Yet another object of the present invention is to provide a portable lighted mirror having a light fixture that sits at the top of the device, flush with the folding panels when in the closed position.

Still yet another object of the present invention is to provide a portable lighted mirror having a sensor between the main panel and the foldable mirror panels and is activated when the panels are moved to an open position.

Another object of the present invention is to provide a portable mirror having easy viewing of feet for people inflicted with diseases such as diabetes.

Additional objects of the present invention will appear as the description proceeds.

The present invention overcomes the shortcomings of the prior art by providing a portable mirror having a plurality of foldable mirror panels, each hingedly attached to a main mirror panel. A light fixture is provided and sits at the top of the device, flush with the folding panels when in the closed position. A sensor is provided between the main panel and the foldable mirror panels and is activated when the panels are moved to an open position. The device provides easy viewing of feet for people inflicted with diseases such as diabetes.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

FIG. 2 A is a rear view of the light fixture of the present invention.

LIST OF REFERENCE NUMERALS

With regard to reference numerals used, the following numbering is used throughout the drawings.
- 10 Present Invention
- 12 Rear Mirror Panel
- 14 Front Mirror Panel
- 16 Base Mirror Panel
- 18 Hinge
- 20 Light Fixture
- 22 Sensor/Switch
- 24 Knob
- 26 Tab
- 28 Carrying Handle
- 30 Light Bulb
- 32 Battery
- 34 Power Cord
- 36 Pivoting Extension
- 38 Finger Notch
- 40 Locking Bar
- 42 Recess

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Figure 1:
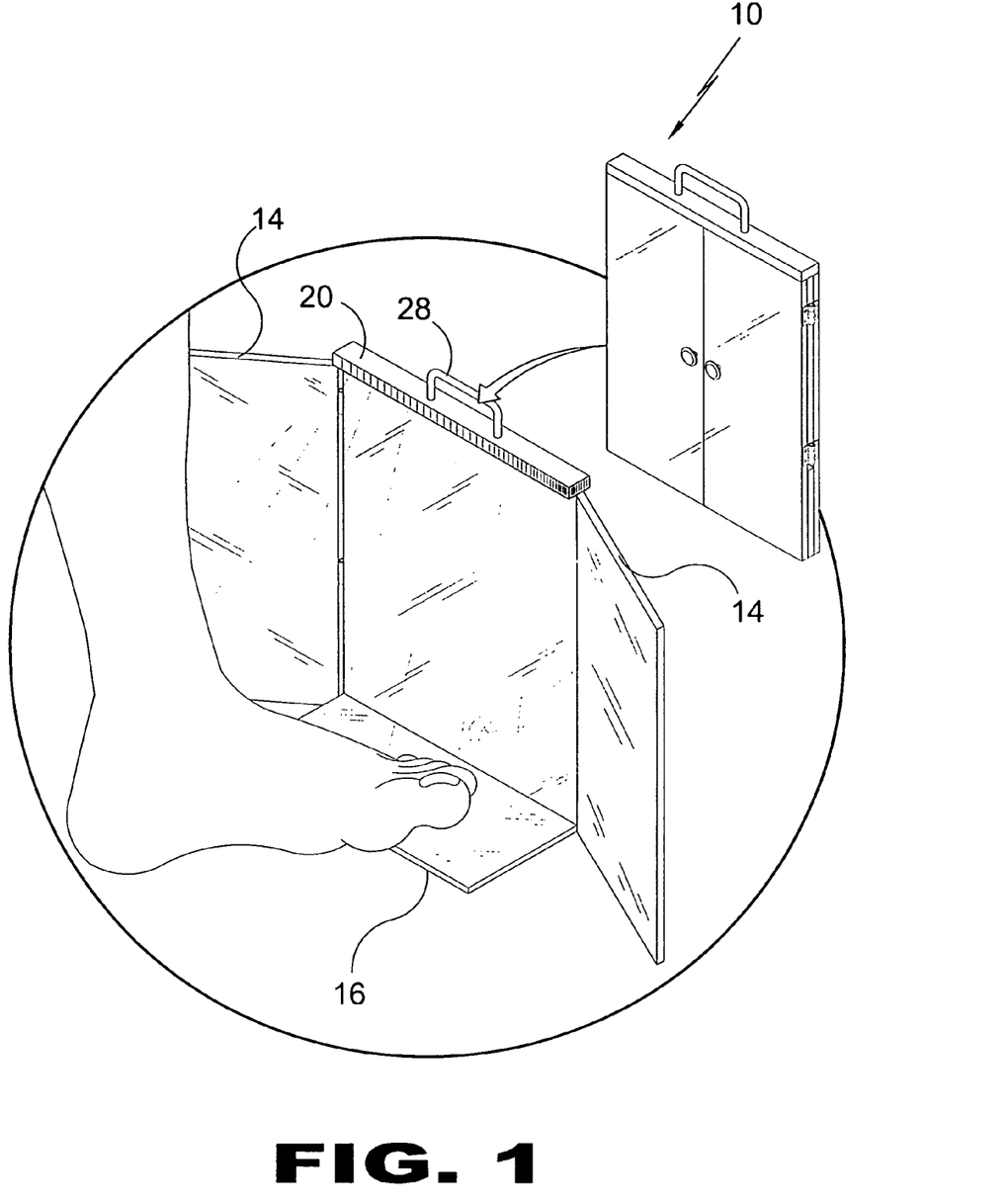
FIG. 1 is an illustrative view of the present invention in use.
Figure 2:
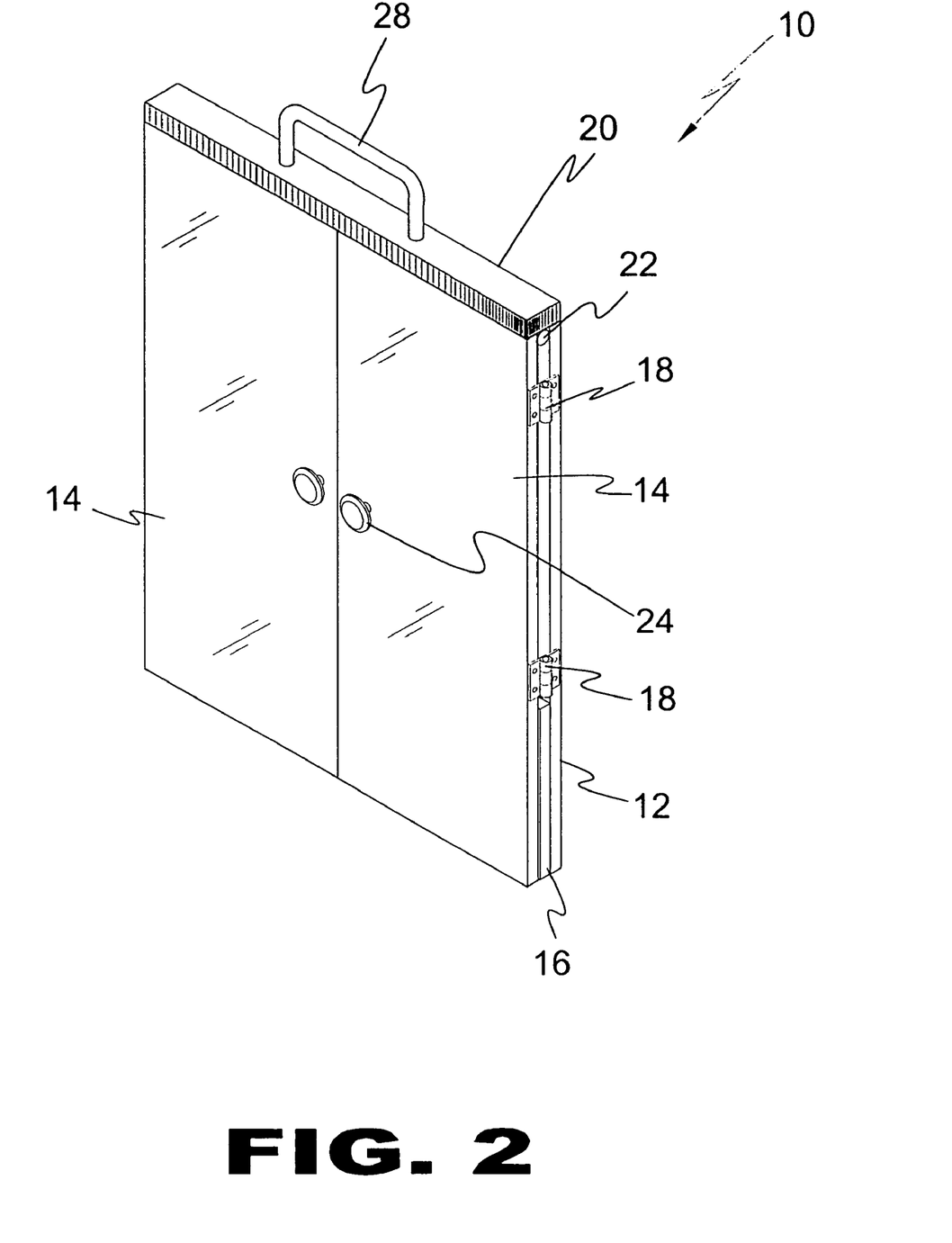
FIG. 2 is a perspective view of the present invention in a folded closed position.
Figure 2A:
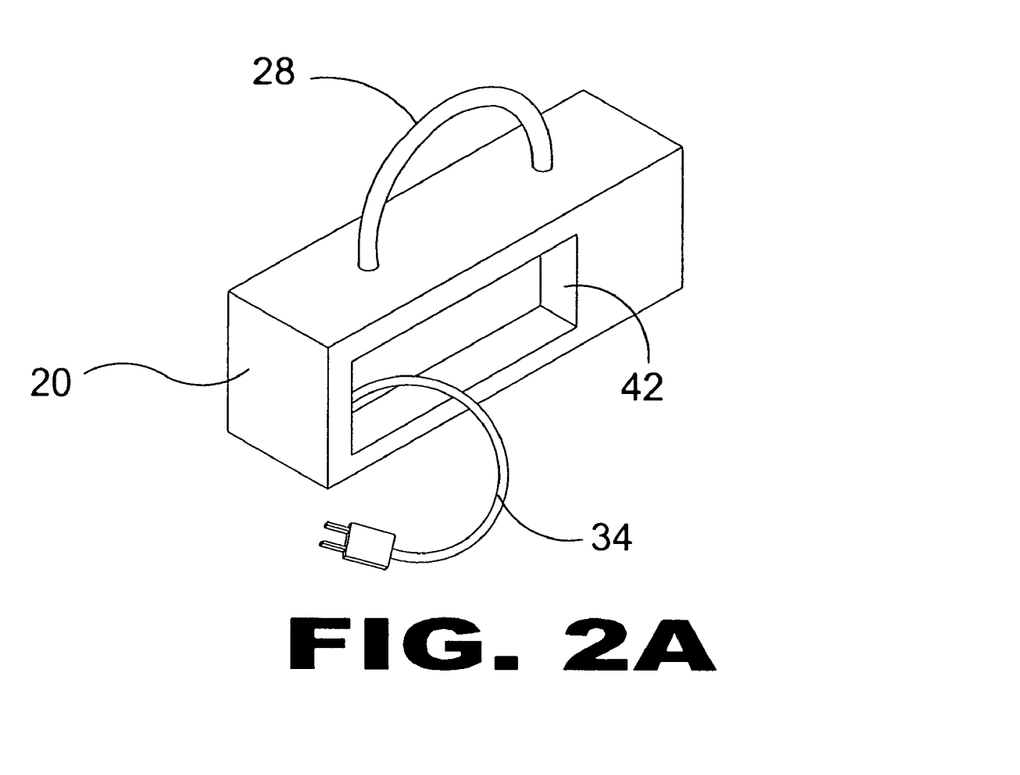
Figure 2B:
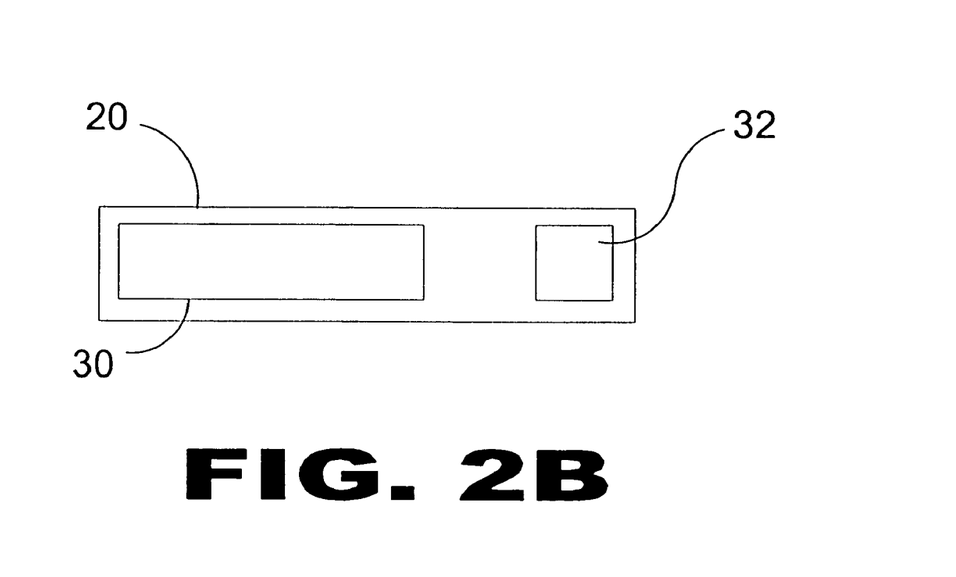
FIG. 2B is a bottom view of the light fixture of the present invention.

Looking at FIG. 1, an illustrative view of the present invention 10 is shown. The present invention is a portable folding mirror. This Figure shows the mirror in both a folded or closed position and an open or in use position. FIG. 2, shows the present invention 10 in the folded or closed position. The portable folding mirror is shown having a two front mirror panels and a base mirror panel, each panel attached to the rear mirror panel 12 by at least one hinge 18. A light fixture 20 is provided which is located at the top of rear panel. A sensor or switch 22 is provided between the rear panel 12 and one or both of the front mirror panels 14. The sensor or switch 22 turns on the light fixture 20 when the front panels 14 are in the open or use position and turns off the light fixture 20 when the front panel 14 is folded over the rear panel 12 in the closed position. The switch 22 can be a contact switch 22. The contact switch 22 will be turned off by contact with a closed front panel 14 and the contact switch 22 will bias to the on position when the front panel 14 is no longer in contact with the switch 22. The sensor 22 could be a proximity sensor 22 that senses the proximity of a front panel when the panel is in the closed position and turns off the light. When the front panel is moved into the open position the sensor 22 no longer senses the panel and the light is turned on by the sensor 22. The sensor or switch 22 completes the electrical circuit. The device provides easy viewing of feet for people inflicted with diseases such as diabetes. Now looking at FIG. 2, the portable mirror is shown in the fully closed position. On the front of the mirror are two front mirror panels 14; each panel being mounted on hinges 18 for folding into both open and closed positions. These front panels 14 are shown in the closed position. On the outer surface of each front panel 14 is a knob 24 to aid the user in moving or folding the front panels 14 into both the open and the closed positions. On the top of the rear panel 12 is a light fixture 20 on which a carrying handle 28 is secured. The light fixture 20 serves several purposes. The light fixture 20 is secured to the rear panel and provides a stable location for the carrying handle 28 disposed thereon. The light fixture 20 contains at least one light bulb 30 (see FIG. 8) for illumination of the user or a part thereof. The light bulb(s) 30 can be light emitting diodes commonly referred to as LED's. The bulb(s) 30 can also be florescent or incandescent depending upon the amount or type of light desired by the user. As seen in FIG. 1, the light fixture 20 is illuminating the users foot. The light fixture 20 is sized so that when the front panels 14 are folded over the rear panel 12 the outer surfaces of the front panels are flush with the outer surface of the light fixture 20. The light fixture 20 can also hold a battery or batteries 32 for providing the light bulb 30 with power. It has also been contemplated that the rear panel 12 could be formed with a hollow area between spaced front and rear surfaces so that a flat and thin battery 32 could be located in the hollow area. It has been contemplated that alternating or a/c current can be employed in lieu of or in combination with a battery or batteries 32. Thus the mirror would be provided with a power cord 34 for a/c power. A/c current could provide power for the light bulb 30 and charge the batteries 32 at the same time. The batteries could be relied upon when a/c power is not available. It is envisioned that the rear of the light fixture 20 can be provided with a recess 42 to store the power cord 34 when not in use. The light fixture 20 can be made of durable lightweight materials such as aluminum, nylon, fiber-reinforced plastic, durable plastics or any other suitable material.

FIGS. 1-9 show individual spaced apart hinges 18 securing the front panels 14 and base panel 16 to the rear panel 12. It is also envisioned that the hinges 18 can be continuous. A continuous hinge 18 would extend from or near the top of a panel to or near the bottom of the same panel. Continuous hinges 44 are typically referred to as piano hinges in the art. They are desirable since they support the two pivoted panels along the entire length of the hinge 18. This will ensure that the panels will not warp or bow along the hinge line. It is also contemplated that either hinge 18 (individual or continuous) can be integrally formed with the mirror panels. One way of accomplishing this is to form the mirror panels of plastic. The hinges 18 can be formed molded at the same time and out of the same material as the mirror panels thus forming joined panels. This type of hinge 18 is typically referred to a living hinge 18 in the art. The hinges 18 could also be formed separately and then bonded to the panels. It this case the hinges 18 can be formed from the same material as the mirror panels or a different material. The advantage of the hinges 18 being formed separately is that they can be formed of a more flexible material than the mirror panels. The hinges 18 can be made of an elastomer, synthetic rubber, natural rubber, silicone, polypropylene, or any other suitable plastic.

Figure 3:
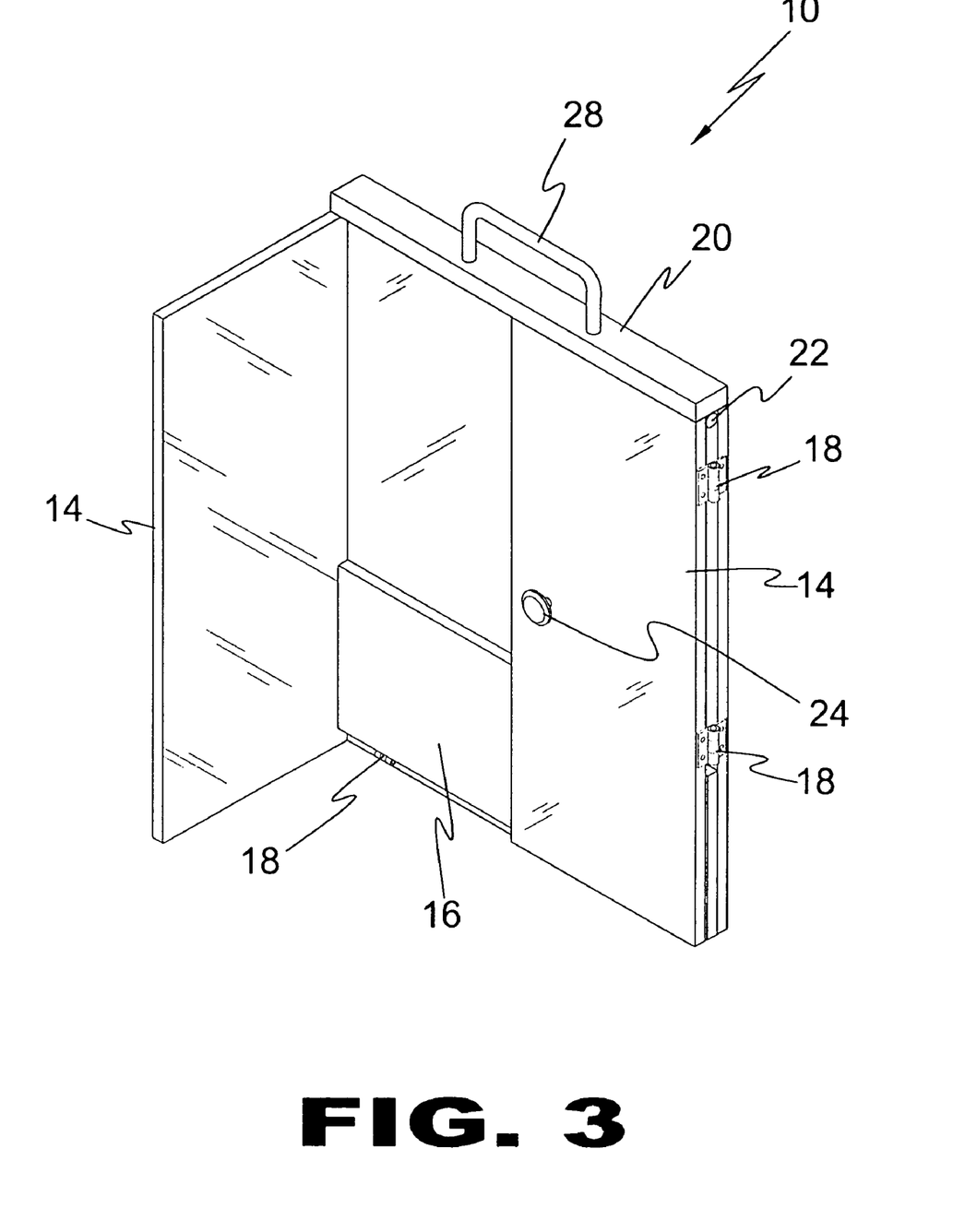
FIG. 3 is a perspective view of the present invention in a partially open position.
Figure 4:
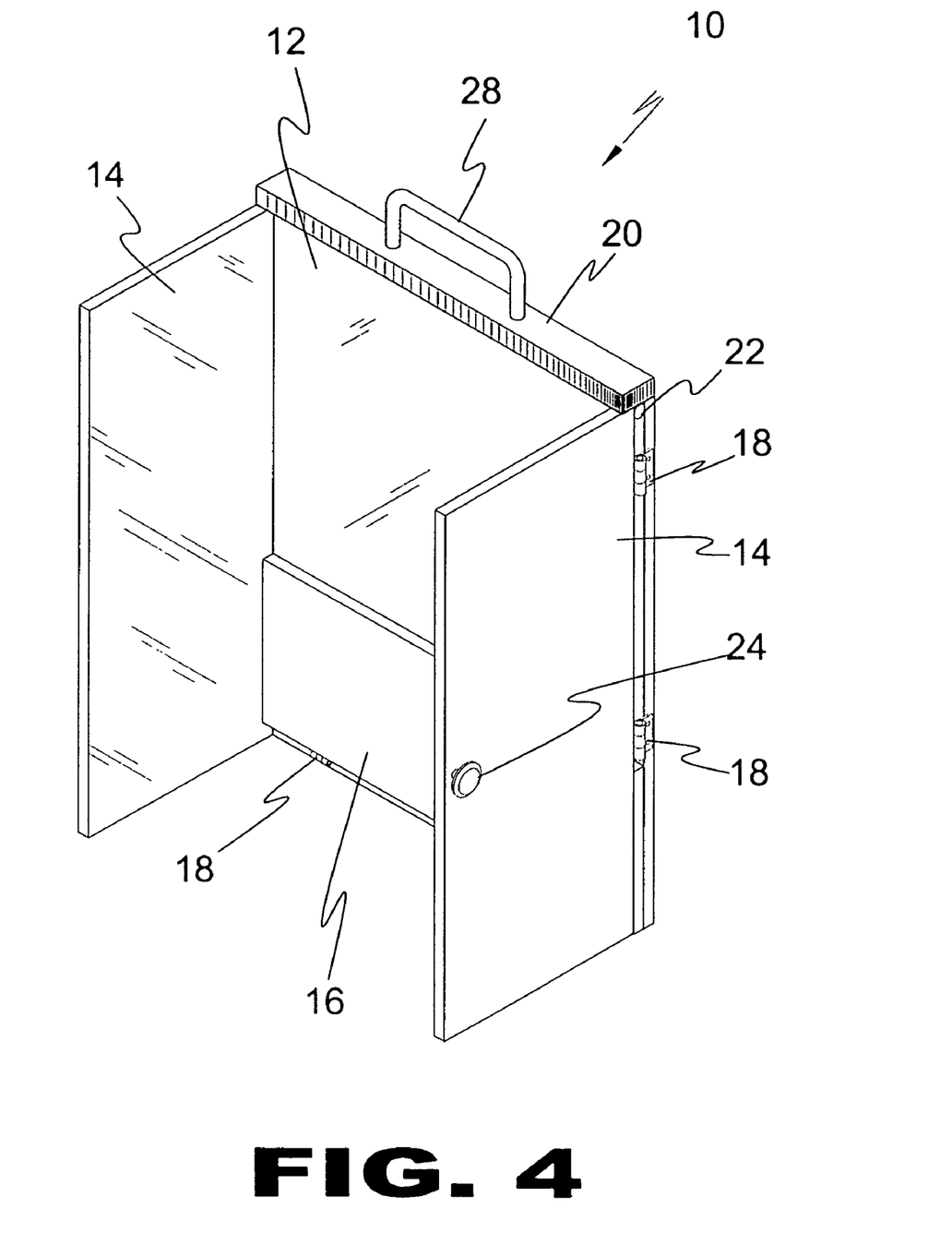
FIG. 4 is a perspective view of the present invention in a partially open position.
Figure 5:
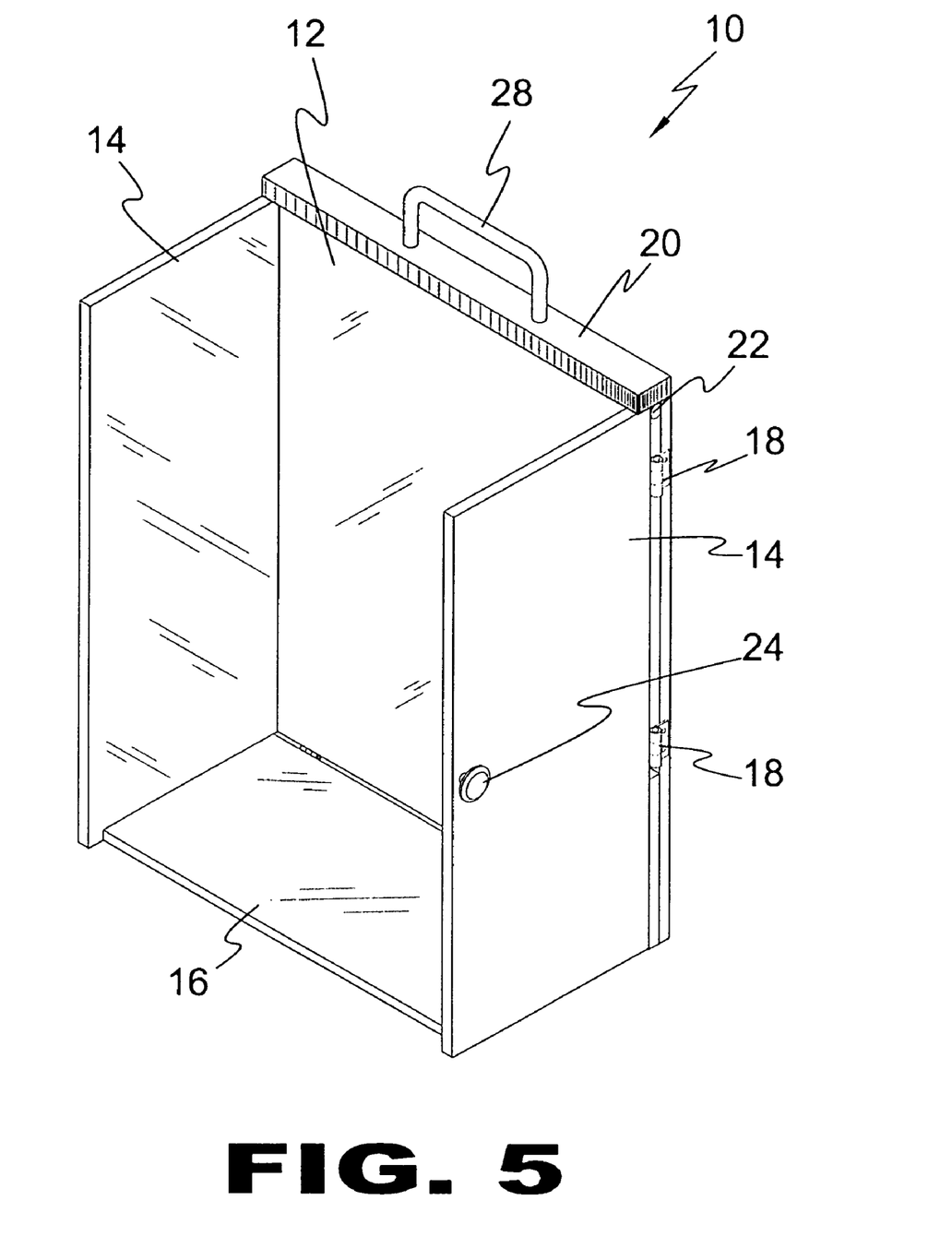
FIG. 5 is a perspective view of the present invention in a partially open position.
Figure 6:
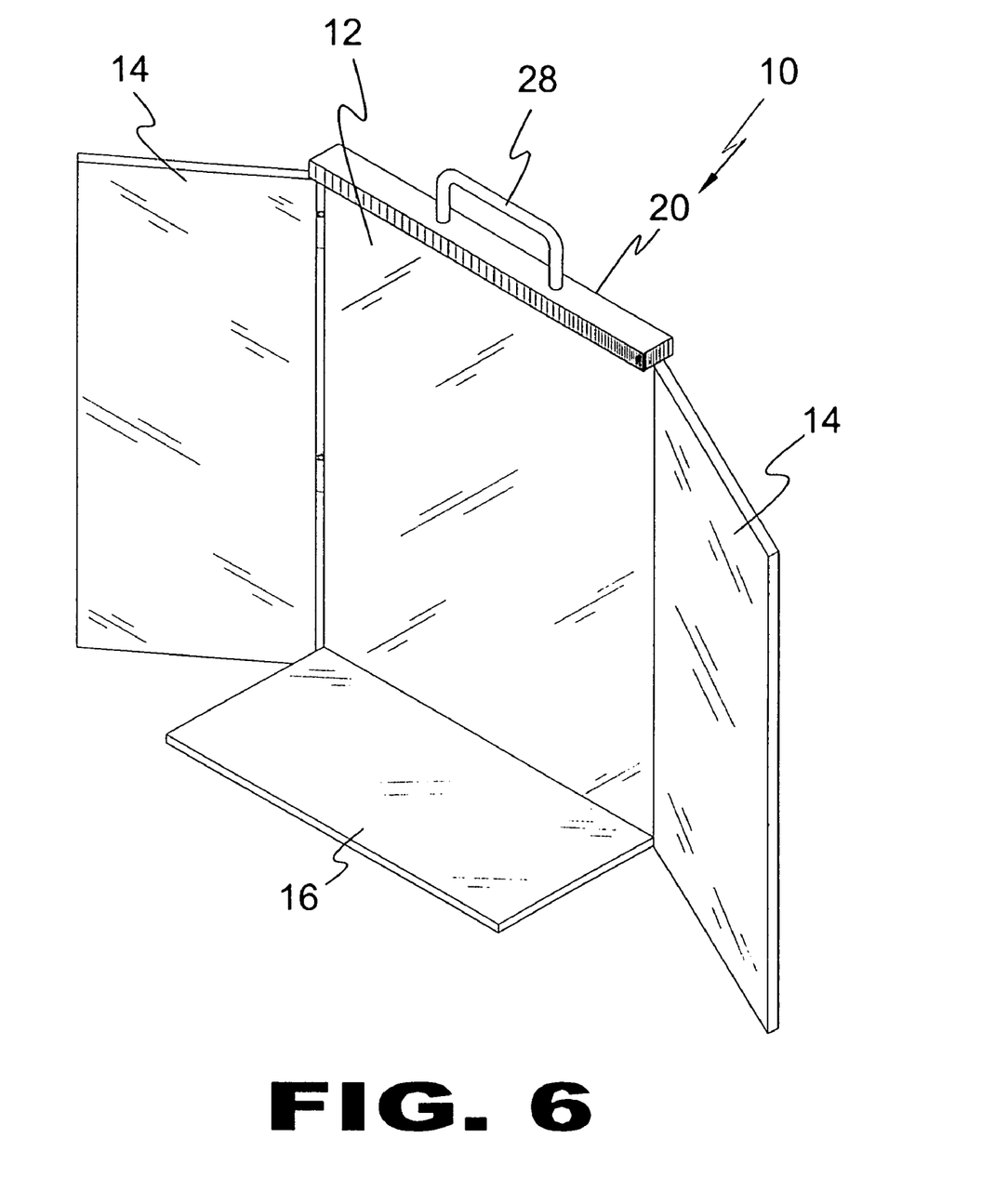
FIG. 6 is a perspective view of the present invention in a fully open position.
Figure 6A:
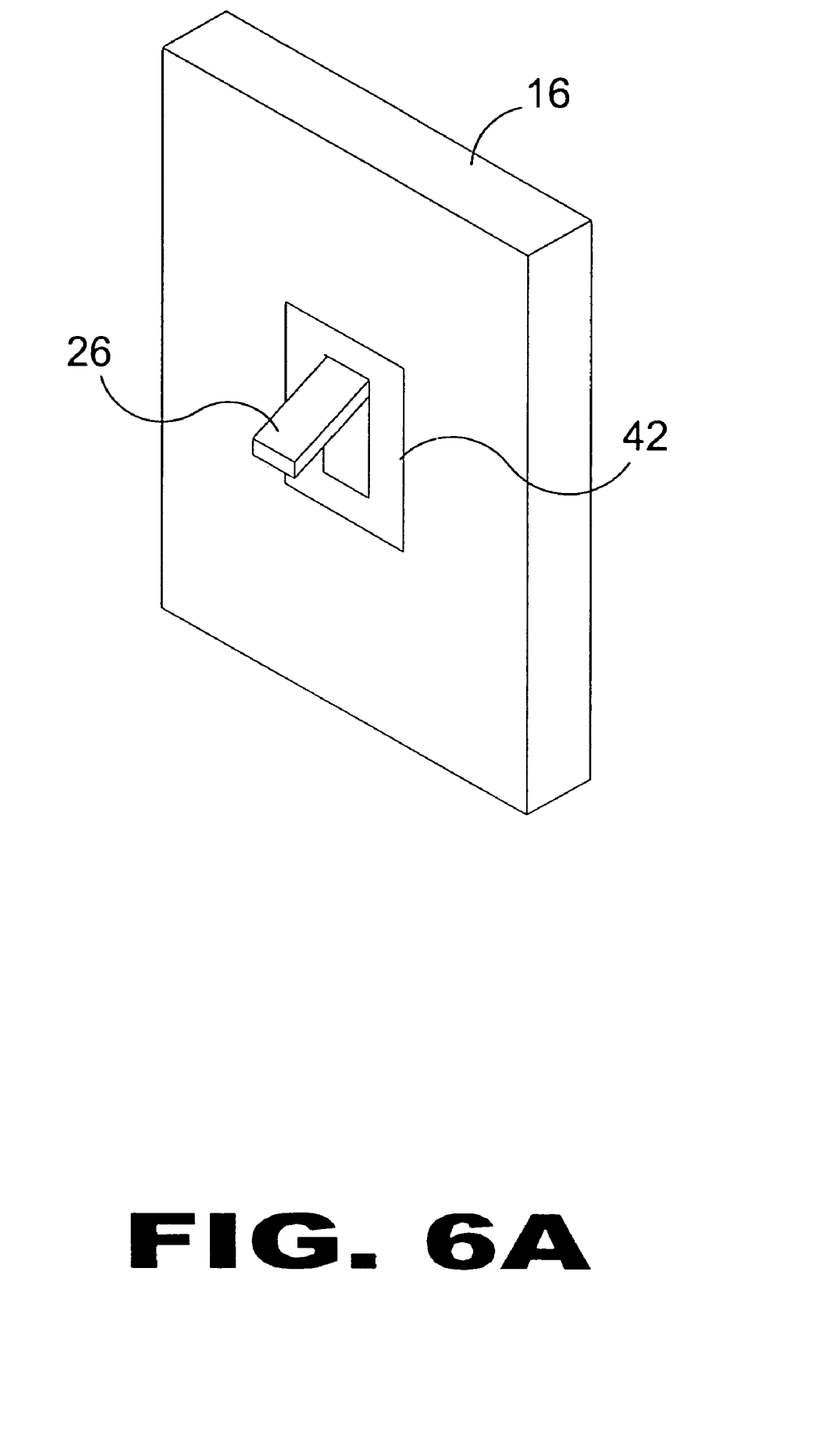
FIG. 6A is a perspective view of the base panel.
Figure 6B:
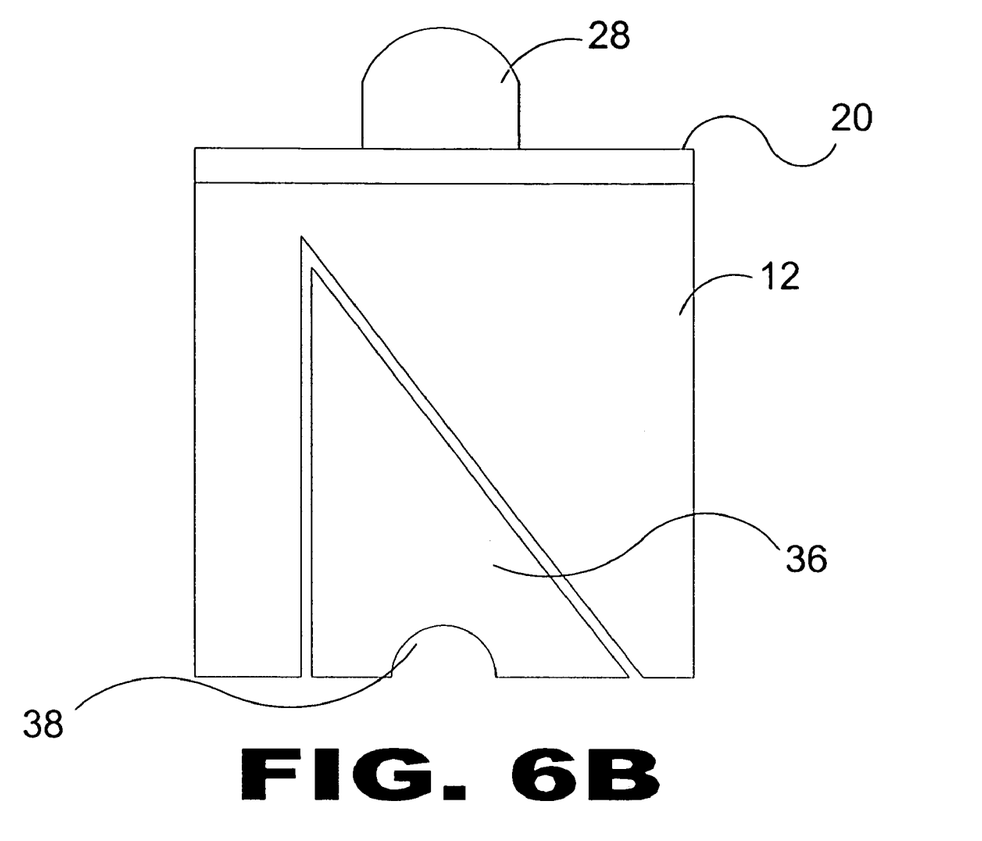
FIG. 6B is a rear view of the light fixture.
Figure 6C:
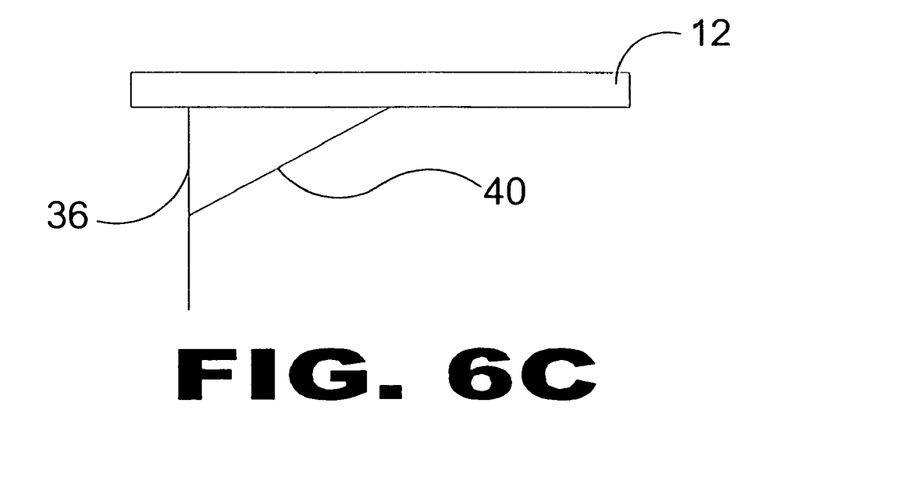
FIG. 6C is a bottom view of the light fixture.

FIGS. 3-6 show how the device opens. It is in FIGS. 3 and 4 the base mirror panel 16 is shown secured to the lower end of the rear panel 12 by a hinge or hinges 18. In this position the base mirror panel 16 is shown in the closed position where it is folded over the rear mirror panel 12. The base panel 16 may have flexible tab 26 to make it easier for the user to position the base mirror panel 16 in the open position (see FIG. 6A). The tab 26 could be a thin flexible member that is attached to base mirror panel 16. The base mirror panel 16 may have a slight recess 42 to in which the tab 26 is received to eliminate any interference with the front mirror panels 14 when the front panels are in the closed position. This tab 26 would be folded and slightly biased to extend out once the front panels 14 have been opened. The Figures show the base panel 16 being shorter than the rear panel 12. If desired the base panel 16 can be made the same size as the rear panels 12. The hinges 18 that secure the front panels 14 to the rear panel 12 must provide for more movement greater than 90 degrees. FIGS. 1 and 6 show the front panels 14 pivoting greater than 90 but less than 180 degrees with respect to the rear panel 12. FIGS. 3-5 show the front panels 14 and base panel 16 are pivoted 90 degrees relative to the rear panel 12. It has also been contemplated that the hinges 18 on the front panels 14 may provide up to 180 degrees or more of movement. The hinges 18 on the base panel 16 need only provide 90 degrees of movement. It has also been considered that the hinges 18 be provided with locking means to maintain the hinges in specific angular positions relative to the rear panel 12. Two of these positions would be the open and closed positions. It may be desirable to provide additional locking positions between the open and closed positions. The locking means could be in the form of a stop to prevent further movement. This could also be in the form of a groove, or notch, or detent in which the hinge rests or stops to prevent the mirror panels from moving relative to each other until enough force is employed by the user to move the hinge 18 beyond the groove, or notch, or detent. The locking hinge feature along with the base panel 16 will maintain the mirror in the up right position. Looking at FIG. 1, the user's foot is shown resting on the base panel 16. In this position, since the hinges are locked into position, the weight of the users foot on the base panel will maintain the mirror in an up right position. It is also possible to provide the rear panel 12 and front panels 14 with pivoting extensions 36 to maintain the mirror in the upright position (see FIGS. 6B and 6C). These pivoting extensions 36 would be flush with the surface of the panels in which they are disposed. They could be accessed by the user via a finger notch 38. They would be extended by the user and locked into position by a locking bar 40 to support the mirror in the upright position. These would function in the same manner as the extensions on a picture frame, which allow the picture frame to stand on a flat surface. The extensions of the present invention can be made such that the front or rear panels are supported at 90 degrees to the surface on which they sit or at a slight angle of approximately 15 degrees or less. This slight angle would angle the top of the mirror away from the user. The slight angle will provide the user with a greater field of view and aid in maintaining the mirror in the upright position.

Figure 7:
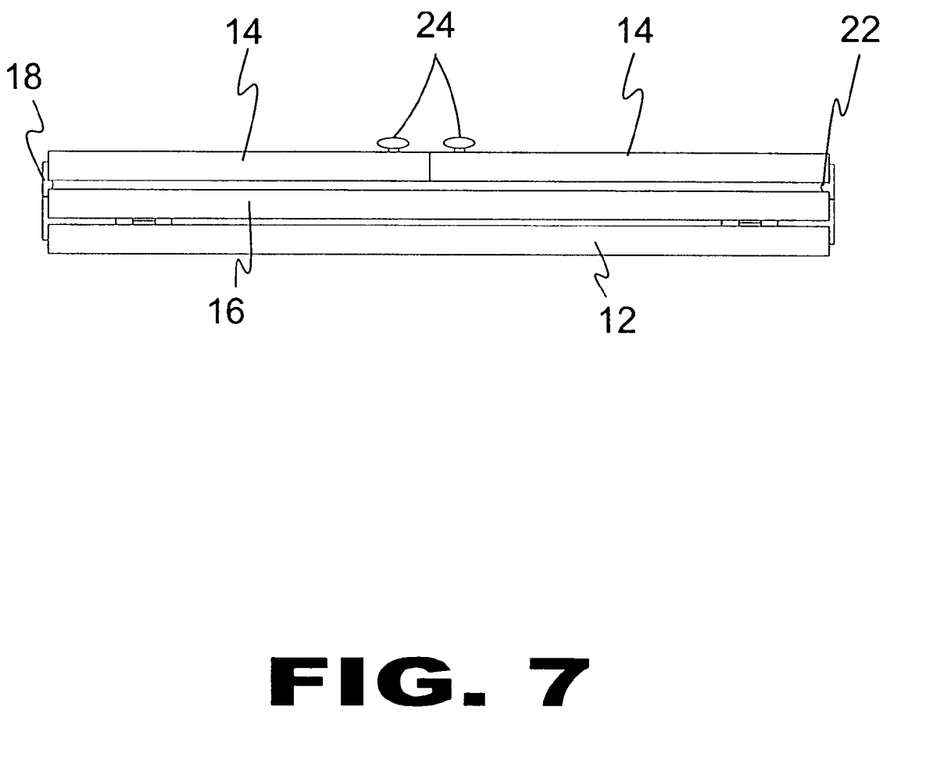
FIG. 7 is a bottom view of the present invention in a fully closed position.
Figure 8:
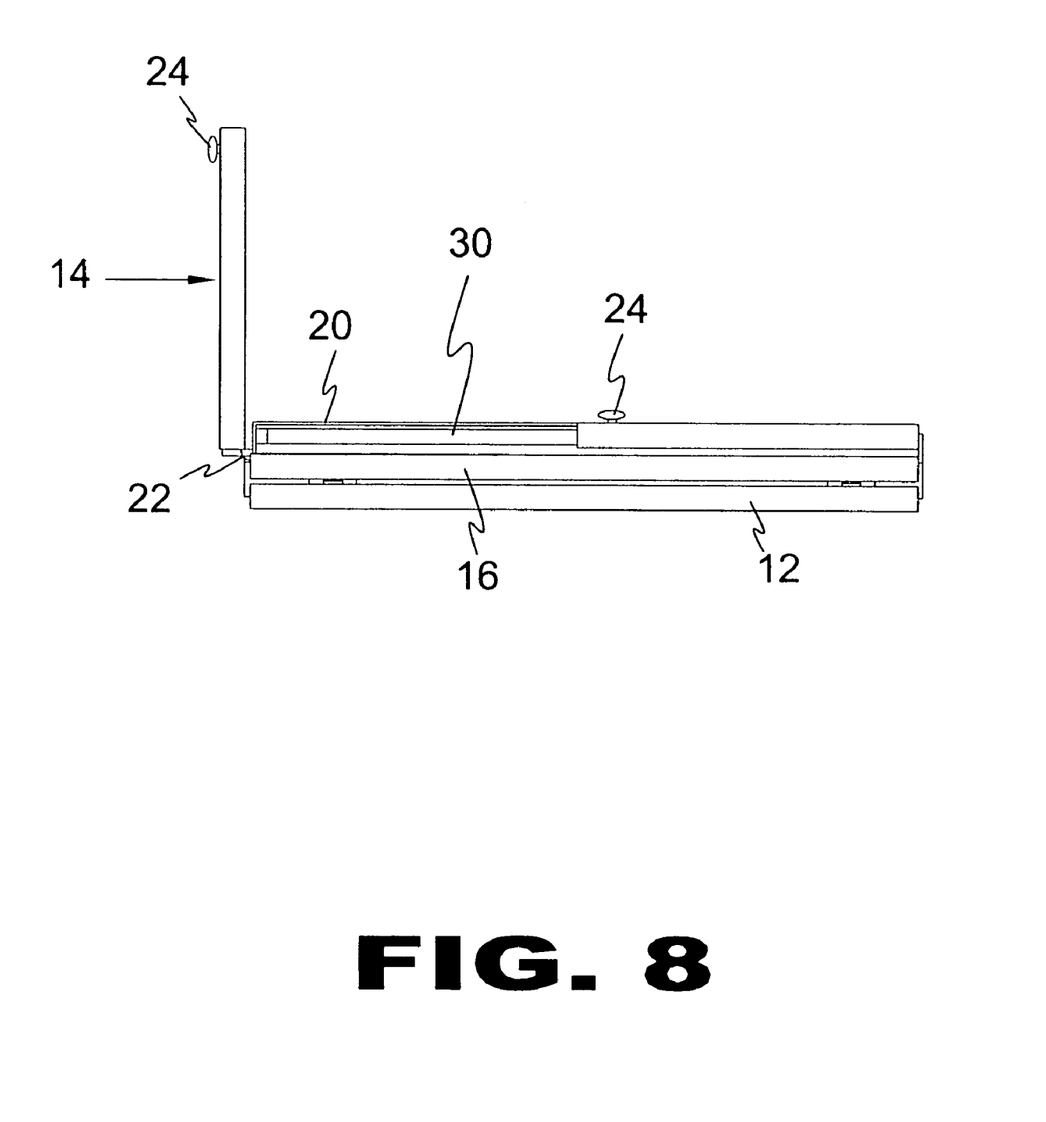
FIG. 8 is a bottom view of the present invention in a partially open position.
Figure 9:
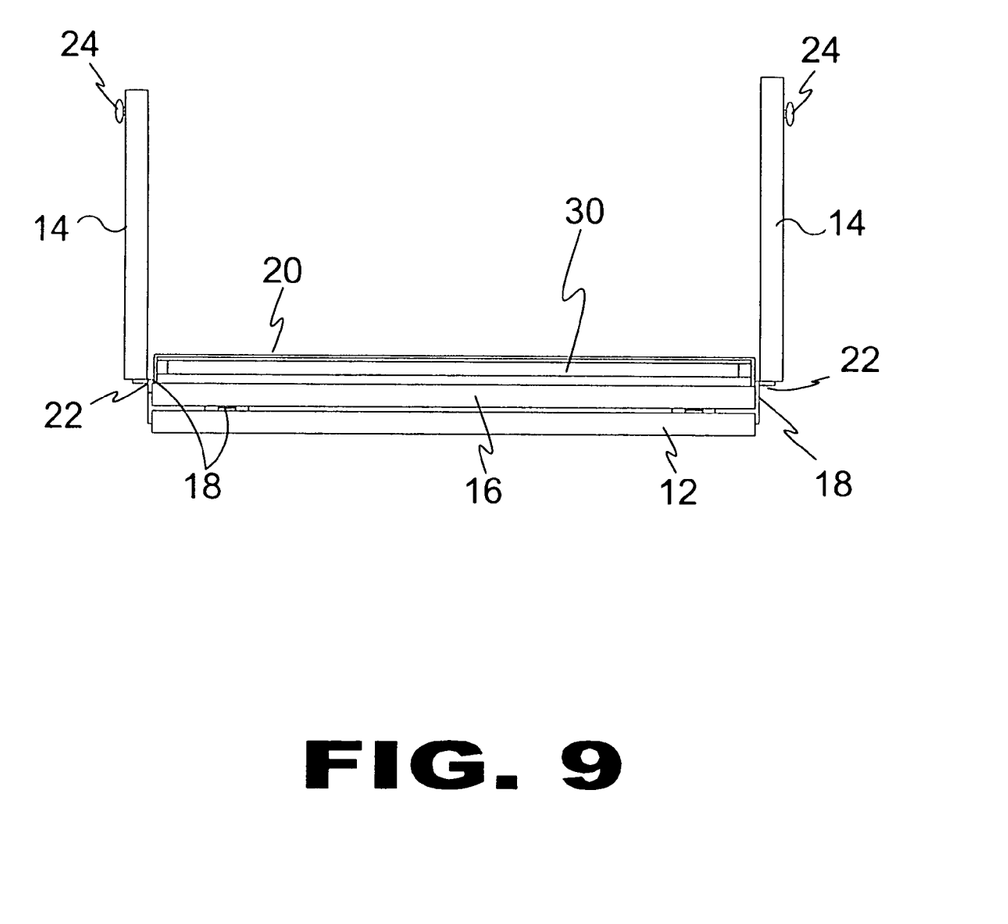
FIG. 9 is a bottom view of the present invention in a partially open position.

FIGS. 7-9 show the bottom view of the present invention. Looking at FIG. 7, the present invention is shown in the closed position. In this view the hinges 18 are seen joining the base panel 16 to the rear panel 12 and the front panels 14 to the rear panel 12. FIGS. 8 and 9 show the underside of the light fixture 20 and the at least one light bulb 30. As seen in the FIGS. 7 and 8 the light bulb 30 is directly visible since there is no cover on the open end of the light fixture 20. It has been contemplated that the light fixture 20 be provided with a cover closing the open end of the light fixture and protecting the light bulb 30. The cover can be made of a durable transparent plastic material.

I claim:

1. A portable folding mirror comprising:
   a rectangular rear mirror panel having top, bottom and side edges,
   a pair of side mirror panels each having top, bottom and side edges,
   each of said side mirror panels being secured to an opposite side of the rear panel by at least one hinge,
   said side mirror panels moveable between an open position and a closed position,
   wherein said side panels are folded over said rear panel in the closed position and where said side panels are folded off of and away from said rear panel in the open position,
   wherein each mirror panel has two opposed surfaces, an inner and outer surface, wherein all of said inner surfaces are mirror surfaces and the inner surfaces of the side panels face the inner surface of the rear panel when said side panels are in the closed position,
   wherein the rear panel has a light fixture secured along a top edge thereof covering all of said side panels when in the closed position and within a housing with a bottom opening for directing light downwardly, wherein a carrying handle is secured to an upper surface of the light fixture housing, and wherein a sensor or switch is positioned adjacent at least one of the side panels such that when said panel is moved into the open position then the light will be turned on and provide illumination to the user,
   each of said side panels covering half of the inner surface of the rear panel when said side panels are in the closed position, with each side panel having a knob on the outer surface thereof for opening said side panels,
   said side panels having side edges thereof hinged to side edges of said rear panel,
   a base mirror panel having an edge hinged to the bottom edge of said rear panel and movable between an open position where said base mirror panel extends horizontally from said rear panel and a closed position where said base mirror panel is folded up against said inner surface of said rear panel and enclosed by said side panels when in the closed position, said base mirror panel having an inner surface which is mirrored and faces said rear panel when in the closed position.

2. The portable mirror of claim 1, wherein the light fixture has at least one light bulb that is powered by a battery.

3. The portable of claim 2, wherein said side panels are able to pivot more than 90 degrees but less than 180 degrees away from the rear panel and the hinge of the base mirror panel allows said base panel to pivot no more than 90 degrees away from the rear panel.

4. The portable mirror of claim 1, wherein the light fixture has at least one light bulb that is powered by an alternating current.

5. The portable mirror of claim 1, wherein the base mirror panel has a tab disposed on an outer surface thereof, said tab being graspable by the user to aid the user in moving the base panel from the closed position to the open position.

6. The portable mirror of claim 5, wherein the rear panel has a pivoting extension disposed on the outer thereof, said pivoting extension moveable from a closed position to an open position, wherein in said open position the pivoting extension supports the portable mirror in an up right position.

7. The portable mirror of claim 6, wherein the pivoting extension is secured into the open position by a locking bar.

* * * * *